United States Patent [19]

VonBargen

[11] Patent Number: 4,842,406

[45] Date of Patent: Jun. 27, 1989

[54] OPTICAL INSTRUMENTS FOR MEASURING PARTICLE SIZES

[75] Inventor: Kenneth P. VonBargen, Berwyn Heights, Md.

[73] Assignee: Pacific Scientific Company, Newport Beach, Calif.

[21] Appl. No.: 144,225

[22] Filed: Jan. 15, 1988

[51] Int. Cl.$^4$ ...................... G01N 21/53; G01N 15/02
[52] U.S. Cl. .................................. 356/336; 356/338; 356/341
[58] Field of Search ............... 356/335, 336, 338, 341, 356/442; 250/564, 565, 574; 377/11

[56] References Cited

U.S. PATENT DOCUMENTS

| | | | |
|---|---|---|---|
| 3,797,937 | 3/1974 | Shofner | 250/564 X |
| 3,830,568 | 8/1974 | Allen. | |
| 4,015,135 | 3/1977 | Tipton, Jr. | 250/564 X |
| 4,265,538 | 5/1981 | Wertheimer. | |
| 4,348,111 | 9/1982 | Goulas et al. | |
| 4,596,464 | 6/1986 | Hoffman et al. | 356/336 |

FOREIGN PATENT DOCUMENTS 1173264 8/1985 U.S.S.R. .

OTHER PUBLICATIONS

"High-Speed Single Particle Sizing by Light Scattering in a Flow System", G. C. Salzman et al., *Society of Photo Optical Instrument Engineering*, vol. 220, Optics in Metrology and Quality Assurance (1980), pp. 23-27.

*Primary Examiner*—Davis L. Willis
*Assistant Examiner*—Matthew W. Koren
*Attorney, Agent, or Firm*—Lane and Aitken

[57] ABSTRACT

In an optical instrument for measuring particles in the size range of 0.5 microns to 300 microns, a laser beam is caused to pass through a sample stream of liquid containing particles to be measured. A photodetector detects a portion of the direct laser beam passing through the sample stream and the amplitudes of the pulses generated by this first photodetector provide a measurement of particles in the size range of 10 to 50 microns. A second photodetector detects forward scattered light from the laser beam passing through the liquid sample stream. The amplitudes of pulses generated by the second photodetector provide a measurement of pulses in the size range of 0.5 microns to 10 microns and the durations of pulses generated by the second photodetector provide a measurement of pulses in the size range of 50 to 300 microns.

11 Claims, 2 Drawing Sheets

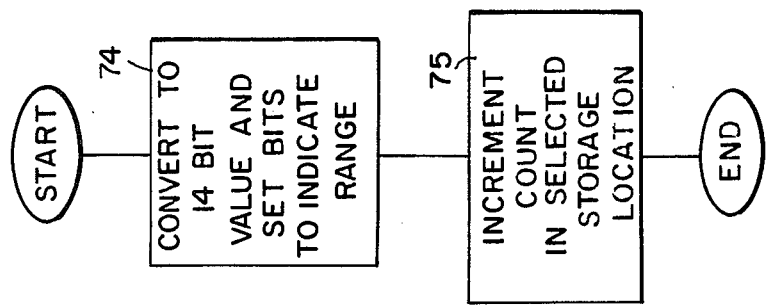
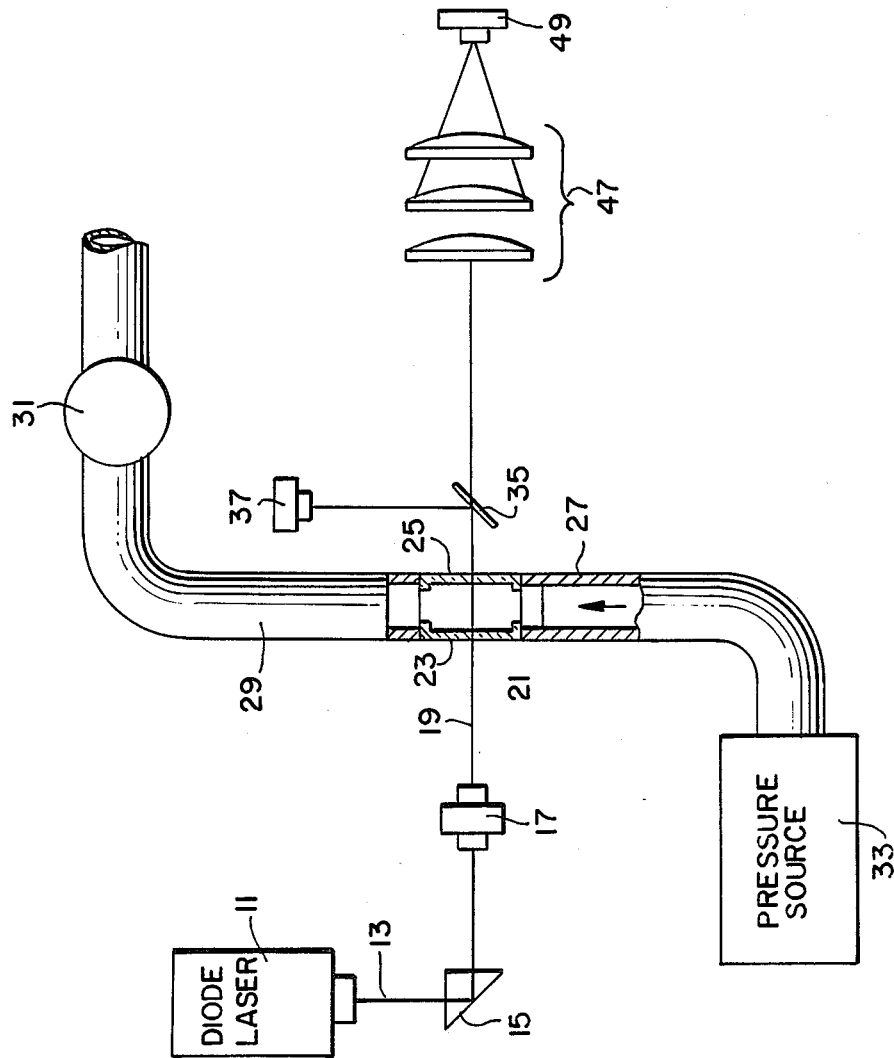

OPTICAL INSTRUMENTS FOR MEASURING PARTICLE SIZES

This invention relates to instruments for measuring the size of particles entrained in a fluid stream and more particularly, to an instrument which measures a wide range of particle sizes by detecting the effect of the particles on a light beam passing through the fluid stream.

Instruments using laser beams to measure particle sizes in the fluid streams exist in the prior art. However, the prior art instruments measure particle size in a relatively limited size range. For example, one instrument marketed by the assignee of this invention measures particles in the size range of 0.5 to 25 microns. The instrument of the present invention improves on this prior art instrument by increasing the range of precise particle size measurement up to 300 microns.

SUMMARY OF THE INVENTION

In the instrument of the present invention, a light beam is shaped into the form of a flat sheet and passed through the fluid stream. One photodetector is positioned to detect the light beam directly. A second photodetector is positioned to detect light scattered from the laser beam as it passes through the fluid stream. Each time a particle passes through the laser beam it will partially obscure the laser beam passing to the photodetector positioned to detect the laser a pulse. Also, each particle will change the scattered light detected by the second photodetector and each particle will cause the second photodetector to generate a pulse. For particles in the size range of 10 microns to 50 microns, the first photodetector will generate pulses having amplitudes which very accurately correlate with particle size. For particles in the size range of 0.5 microns to 10 microns, the second photodetector will generate pulses having amplitudes which correlate very well with particle size. For particles in the size range of 50 microns to 300 microns, the second photodetector will generate pulses having pulse lengths which correlate very well with particle size.

In accordance with the invention, the amplitude of each pulse generated by the first photodetector and second photodetector is converted to a digital value and applied to a microprocessor and the length of the pulse generated by the second photodetector is also converted to a digital value and applied to the microprocessor. If the particle size is in the range of 10 microns to 50 microns, then the digital value generated from the amplitude of the corresponding pulse generated by the first photodetector is used by the microprocessor as an indication of the size of the particle. If the particle size is in the range of 0.5 to 10 microns, the microprocessor uses the digital value obtained from the amplitude of the pulse from the second photodetector to provide an indication of the size of the particle. If the particle size is in the size range of 50 to 300 microns, the microprocessor uses the digital value generated from the length of the pulse generated by the second photodetector to indicate the size of the particle. In this manner, a highly accurate measurement is obtained of the particles in the fluid stream from 0.5 microns in size up to 300 microns in size.

Accordingly, an object of the present invention is to provide an improved instrument to measure particle size in a fluid stream.

Another object of the present invention is to provide an instrument which will measure particle size in a fluid stream over a wide range of particle sizes and with a high degree of accuracy.

Further objects and advantages of the present invention will become apparent as the following detailed description of the invention unfolds and when taken in conjunction with the drawings.

BRIEF DESCRIPTION OF THE DRAWINGS

FIG. 1 schematically illustrates the optical system of an instrument in accordance with the present invention;

FIG. 3 is a flow chart illustrating a program employed in the microprocessor of the block diagram of FIG. 2;

DESCRIPTION OF SPECIFIC EMBODIMENTS

Figure 2:
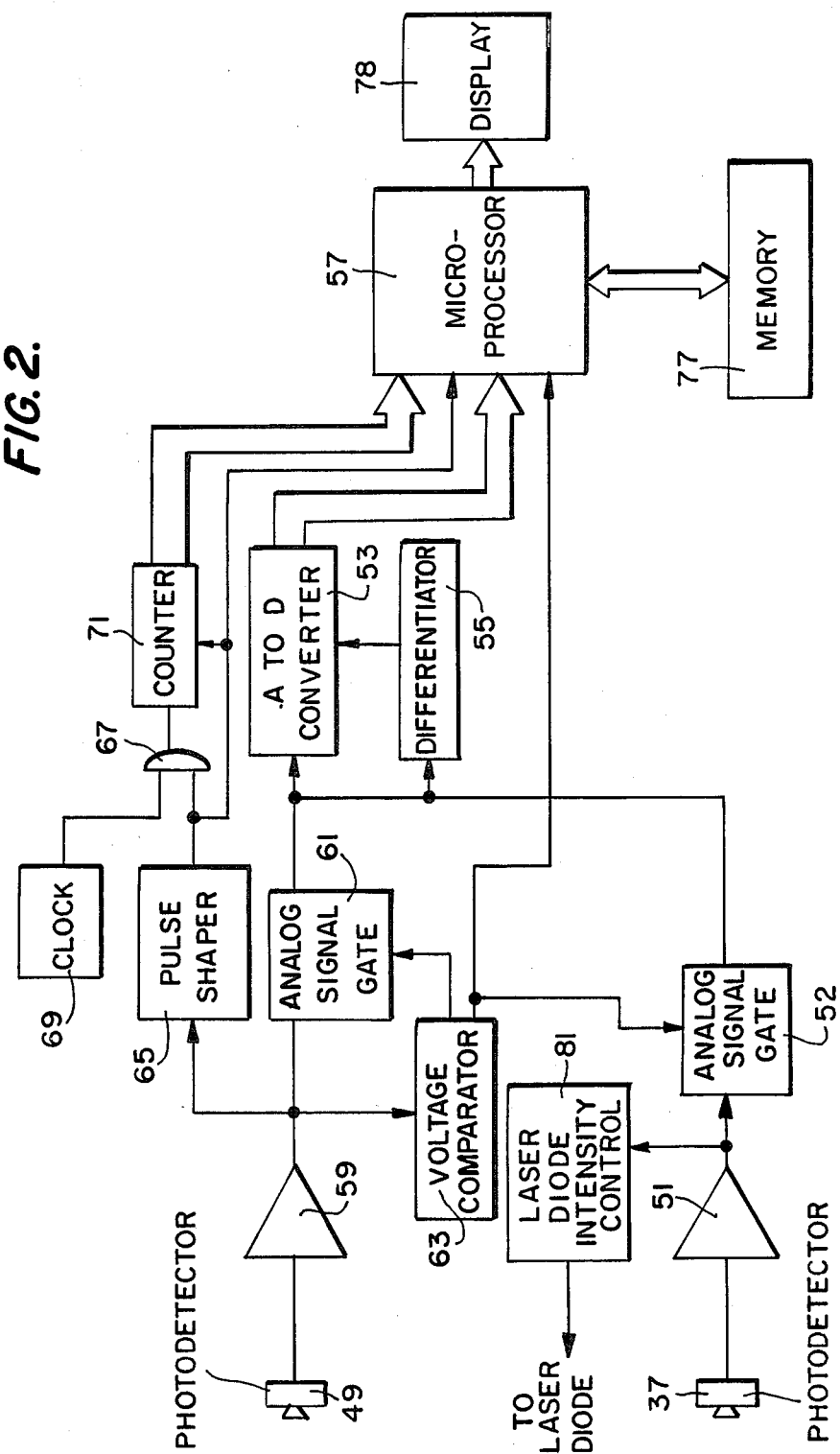
FIG. 2 illustrates a block diagram of circuitry for converting pulses produced by the photodetectors of the system shown in FIG. 1 into particle size measurements.

As shown in FIG. 1, in the instrument of the present invention, a laser diode 11 generates a collimated laser beam 13 which is reflected by a prism 15 to a beam expander 17. The beam expander 17 shapes the received laser beam into the form of a thin flat sheet 19, which in the preferred embodiment is 500 microns wide and 35 microns thick. The flat sheet-like beam is transmitted through a transparent window 21 of a test chamber 23, which is arranged to have a sample stream of fluid to be tested flowing upwardly through the test chamber. In the specific embodiment, the fluid is liquid but the invention is also applicable to measuring the size of particles entrained in gases. The laser beam 19 encountering any particles in the fluid flowing through the chamber 23 will be partially forward scattered by such particles, and the forward scattered rays as well as the portion of the laser beam which is not scattered will pass through an exit window 25 of the sample chamber. An inlet conduit 27 leads the sample stream to be measured into the test chamber 23 and an outlet conduit 29 carries the fluid flowing through the test chamber away to a flow rate control valve 31. The flow rate valve 31 controls the rate of fluid flow through the chamber 23 precisely to be a constant which is important for accurate particle size measurements. A sample liquid stream is caused to flow through the conduits 27 and 29 and the chamber 23 by a pressure generated in the stream by a pressure source 33, which may be a pump, a head of the liquid, or by the manner in which the sample stream is collected from a flowing larger stream.

The direct beam 19 passing through the test chamber 23 without scattering is applied to a reflector 35, which reflects of the direct beam to a photodetector 37. The light from the laser beam forward scattered by particles in the sample stream flowing through the sample chamber 23 passes around the beam reflector 35 to the lens system 47 which focuses the forward scattered light on the photodetector 49. Each time a particle passes through the laser beam, it will cause a burst of scattered light which will be detected by the photodetector 49 and cause the photodetector 49 to produce a pulse. Also, each time a particle passes through the laser beam in the test chamber 23, it will partially occlude the direct laser beam and thus, affect the amount of the energy of the the direct laser beam being received by the photodetector 37. As a result, the photodetector 37 will also generate a pulse in response to each particle passing through the laser beam.

It has been determined that particles in the range of 10 microns to 50 microns with a laser beam having a shape as described above will cause the photodetector 37 to generate pulses having amplitudes which correlate precisely with the particle size. It has been further determined that scattered light caused by each particle passing through the laser beam by particles in the range of 0.5 microns to 10 microns will cause the photodetector 49 to generate a pulse having an amplitude which correlate very highly with the particle size. It has been further determined that the scattered light produced as a result of particles in the range of 50 to 300 microns in size upon being detected by the photodetector 49 will generate pulses having a pulse lengths which correlates very highly with the particle size. Accordingly, in the preferred embodiment of the instrument, to measure particle sizes most precisely in the entire range of 0.5 microns to 300 microns, the instrument measures particles in the size range of 0.5 microns to 10 microns by the amplitudes of the corresponding pulses generated by the photodetector 49 in response to the scattering caused by such particles, measures particles in the size range of 10 microns to 50 microns by the pulse amplitudes of the corresponding pulses generated by the photodetector 37 in response to the particles passing through the laser beam, and measures particle size of particles in the range of 50 to 300 microns by the corresponding pulse lengths of pulses generated by the photodetector 49 in response to the scattering from such particles. In order to measure the particle size accurately, particularly of the particles in the range of 50 to 300 microns, the rate of fluid flow through the sample chamber 23 must be kept precisely constant and this constant fluid flow is maintained by the flow rate valve 31.

As shown in FIG. 2, the pulses generated by the photodetector 37 are amplified by an amplifier 51 and applied to an analog signal gate 52. The pulses generated by the photodetector 49 are amplified by an amplifier 59 and applied to an analog signal gate 61 and also to a voltage comparator 63. The voltage comparator 63 compares the amplitude of the applied pulse with a voltage value selected to correspond to the amplitude of a pulse which will be produced by the amplifier 59 in response to a particle 10 microns in diameter. If the voltage comparator 63 detects that the voltage is below this level, the voltage comparator 63 enables the analog gate 61. If the voltage comparator 63 determines that the applied voltage is above this level, it will enable the analog signal gate 52. Accordingly, between pulses, the comparator 63 will enable analog signal gate 61. When a pulse is applied to the comparator 63, the comparator 63 will continue to enable gate 61 unless and until the amplitude of the pulse rises above the value corresponding to a particle 10 microns in diameter. When the pulse voltage exceeds this value, the comparator 33 disables gate 61 and enables gate 52. The gate 61, when enabled, passes the applied pulse to an analog-to-digital converter 53 and to a differentiator 55. Similarly, the gate 52, when enabled, will pass the applied pulse to the analog to digital converter 53 and the differentiator 55. In this manner, output pulses of the amplifier 59 caused by particles up to 10 microns in size are applied to the A-to-D converter 53 and the differentiator 55 and output pulses of amplifier 51 caused by particles greater than 10 microns in size, by the time they reach their peaks, are applied to A-to-D converter and the differentiator 55. In the preferred embodiment of the invention, the analog-to-digital converter 53 is a high speed analog-to-digital converter and the amplitude of the pulse is measured at its peak. To achieve this measurement the differentiator 55 is employed. The differentiator 55 will generate a pulse at the peak of the applied pulse and this pulse is applied to the analog-to-digital converter 53 to signal the analog-to-digital converter 53 to convert the applied pulse amplitude to a digital value. In this manner, the analog-to-digital converter converts the amplitude of the applied pulse at its peak to a digital value, which is applied to a microprocessor 57.

If the particle causing the pulse applied to the A-to-D converter is less than 10 microns in diameter, then the pulse measured by the output of the A-to-D converter 53 and applied to the microprocessor 57 will have originated from the photodetector 49. If the particle is in the range of 10 to 50 microns, then the pulse measured by the digital value applied to microprocessor 57 by the A-to-D converter 53 will have originated from the photodetector 37. The voltage comparator 63 will apply a signal to the microprocessor 57 indicating whether the digital value represents the size of a particle greater or less than 10 microns in diameter. The scale with which the digital value produced by the A-to-D converter represents particle size will be different for pulses originating from the photodetector 49 and caused by particles of less than 10 microns in diameter than for pulses originating from detector 37 and caused by particles in the range of 10 to 50 microns. The analog to digital converter 53 produces a 16 bit digital output value. When the pulse originates from the photodetector 49, the scale of the digital value is such that the maximum 16 bit value represents a particle a little larger than 10 microns in diameter. When the pulse originates from the photodetector 37, the scale of digital value is such that the maximum 16 bit value represents a particle a little larger than 50 microns in diameter.

The amplified output of the amplifier 59 is also applied to a pulse shaper 65 which converts each applied pulse generated by the photodetector 49 in response to a particle into a constant amplitude pulse, which is applied to a gate 67 to enable the gate 67. The gate 67 also receives pulses from a 10 megahertz clock pulse source 69 and when enabled passes these clock pulses to a counter 71. The rising edge of each pulse produced by the pulse shaper 65 resets the counter 71 to 0. The gate 67 will be enabled for the length of the pulse produced by the pulse shaper 65 and pass the applied clock pulses gate to be counted by the counter 71. The count registered by the counter 71 at the end of the pulse produced by the pulse shaper 65 will correspond to the length of the pulse and accordingly, will also correspond to the length of the pulse produced by the photodetector 49. The trailing edge of the pulse produced by the pulse shaper 65 will signal the microprocessor 57 to receive the count in the counter 61. The counter 71 is a 16 bit counter and the 10 megahertz clock scales the count in the counter so that the maximum count that can be stored in the counter will represent a particle having a diameter of about 300 microns.

Thus, each particle passing through the laser beam will cause digital values to be generated by the A-to-D converter 53 and the counter 71. These values are applied to and received by the microprocessor 57.

The microprocessor 57 is programmed to convert received digital value from the A-to-D converter 53 or the counter 71 to a 14 bit value represented in the 14 least significant bit positions of a 16 bit number. The two most significant bit positions are used to indicate whether the binary value is in the range of 50 to 300 microns as represented by a digital value received from the counter 71, represents a particle in the size range of 10 to 50 microns as represented by a digital value received from the A-to-D converter 53 produced in response to a pulse received from the photodetector 37, or represents a particle size less than 10 microns as represented by a digital value received from the A-to-D converter 53 produced in response to a pulse produced by the photodetector 49. In addition, when the digital value from the A-to-D converter is in response to an output pulse from the photodetector 49 indicating that the particle size is less than 10 microns, a floating point conversion is carried out. In the floating point conversion, if the output value of the A-to-D converter is $2^{14}$ or greater, the two least significant bits are discarded and the values in the $2^2$ through $2^{15}$ bit positions are shifted down to occupy the bit positions $2^0$ through $2^{13}$. At the same time the two most significant bits are set to 01 to indicate that the scale of the digital value is such that the maximum 14 bit value will represent a particle size of a little larger than 10 microns. If the output value from the A-to-D converter 53 in response to a pulse from the photodetector 49 is less than $2^{14}$, then the bit values are left in their original positions as received from the A-to-D converter and the two most significant bit positions, $2^{15}$ and $2^{1u}$, are left at 00 to indicate that the scale of the 14 bit values is such that the maximum 14 bit value corresponds to a particle a little larger than 2.5 microns. If the digital value received from the A-to-D converter 53 is in response to a pulse produced by the photodetector 37 indicating that the particle being measured has a size of 10 to 50 microns, then the 16 bit values received from the A-to-D converter are shifted into the $2^0$ through the $2^{13}$ bit positions and the 2 most significant bit positions are set to 10 to indicate that the digital value represents a particle in this size range scaled so that the maximum 14 bit value represents a particle a little greater than 50 microns in size. If the digital value is received from the counter 71, then the microprocessor 57 shifts the 14 most significant values of the count into the $2^0$ to the $2^{13}$ bit positions and the two most significant bit positions are set to 11 to indicate that the particle size in the range of 50 to 300 microns and is scaled accordingly.

The output of the amplifier 51 is applied to a laser diode intensity control circuit 81 which applies a signal to the laser diode 11 to control the intensity of the laser beam generated thereby in response to the output voltage of the amplifier 51 when no particle is passing through the measurement chamber 23. As explained above, each time the particle passes through the measurement chamber 23, it will partially occlude the direct laser beam and thus, cause the photodetector 37 to generate a pulse. When no particle is passing through the laser beam, the laser beam will not be occluded and the resulting voltage value produced by the amplifier 51 will correspond to the laser beam intensity. This voltage value is used by the control circuit to adjust the intensity of the laser beam so that the output voltage of the amplifier 51 is at a constant selected value when no particles are passing through the laser beam. In this manner the intensity of the laser beam generated by the laser diode is maintained essentially constant.

The program controlling the microprocessor 57 is illustrated by the flow chart in FIG. 3. As shown in FIG. 3, each new set of digital values applied to the microprocessor 57 in response to a particle starts the program and causes it to enter into instruction sequence 74, in which the microprocessor selects the digital value from the counter 71 or the A-to-D converter 53 as the particle measurement depending upon the size of the particle as indicated by the received digital values. The microprocessor then shifts the bits into the proper bit positions, and sets the two most significant bits as described above. The program then enters instruction sequence 75 in which the microprocessor increments a count in a storage location in memory 77 corresponding to the 16 bit digital value produced in instruction sequence 74, in which the 14 least significant bits indicate particle size and the two most significant bits indicate scale. A separate memory location in the memory 77 is assigned to each digital value that can be represented by the 16 bits. This arrangement thus requires about 65,000 memory locations. In this manner, the microprocessor increments a count in a different memory location for each incrementally different particle size as determined by the digital values generated by the A-to-D converter 53 and the counter 71 for particles ranging in size from 0.5 microns to 300 microns.

At the completion of a measurement of a fluid sample over a period of time, the microprocessor 57 will display the digital counts in the memory 77 on a display 78 and thus provide an indication of the number of particles of each different incremental particle size throughout the range of 0.5 to 300 microns.

The particle sizes do not correlate in a precisely linear fashion to the digital values generated by the digital converter 53 or the counter 71. Thus, each increment in any one of these digital values does not represent the same increment in particle size, although the digital values produced by the A-to-D converter 53, are close to a linear correlation with the particle size for particles in the range of 10 to 50 microns. To obtain precise measurements, the instrument is calibrated by test particles of known sizes so that each storage location in the memory 77 is determined to represent a known particle size. The microprocessor in displaying the counts in the memory 77 as representing the number of particles in given particle sizes, provides a complete and accurate record of the number of particles in the fluid stream at each size increment.

As explained above, the above described instrument makes use of the fact that a high correlation is provided between the pulse amplitude produced by the photodetector detecting the direct laser beam and particles in the size range of 10 to 50 microns which partially occlude the laser beam. However, very good correlation is also provided between the amplitudes of pulses generated by scattered light and particles in the size range of 10 to 25 microns and very good correlation is provided between the length of pulses generated by scattered light and particles in the range of 25 to 50 microns. Accordingly, in an alternative embodiment of the instrument, the photodetector 37 and the corresponding measurement channel is eliminated and the microprocessor 57 is programmed to measure particles in the size range of 0.5 microns to 25 microns in response to the digital output produced by the A-to-D converter 53 in response to pulses from the photodetector 49 and is programmed to measure pulse particle sizes in the range of 25 to 300 microns by the counts generated by the counter 71.

In a less expensive instrument, than that described with reference to FIG. 2, instead of using a high speed A-to-D converter, which is triggered to make the analog to digital conversion at the peak of each pulse, the pulses could be converted into digital values by comparing the pulse amplitude to voltage reference levels. In such an analog-to-digital conversion, a digital value representing the amplitude is determining by detecting which reference voltage levels the pulse exceeds compared to which voltage reference levels the pulse does not exceed and incrementing a corresponding memory location in response to each pulse. Because of practical limitations on the number of reference voltage levels that can be provided, this latter system of analog to digital conversion provides much less resolution between the measured pulse amplitudes than the instrument illustrated in FIG. 2.

In the preferred embodiment of the invention as described above, the light beam is generated by a laser. However, the particle size also can be measured by using a light beam generated by conventional light source. The light may be visible light, ultraviolet light, or infrared light and the term "light" as used herein means light that can be operated on by conventional optic elements or in other words, light in the range of 180 nanometers to 1800 nanometers in wave length. The above described instrument conveniently makes use of forward scattered light to measure a particle size in specific particle size ranges. Alternatively, instead of using forward scattered light to make these measurements, sideways scattered light, back scattered light, or combinations of light scattered in different directions may be employed to make the measurements in the ranges as described above.

These and other modifications of the specific embodiment of the instrument described above may be made without departing from the spirit and scope of the invention, which is defined in the appended claims.

What is claimed is:

1. An instrument for measuring a wide range of size of particles in a fluid, comprising a means to define a sample stream of fluid containing particles to be measured, means to direct a light beam through said sample stream, photodetecting means to detect light scattered from said beam in response to particles in said sample stream passing through said beam to generate a pulse in response to each particle passing through said beam, measuring means to measure the amplitude of each pulse produced by said photodetecting means and the length of each pulse produced by said photodetecting means, the amplitudes of the pulses produced by the photodetecting means providing measurements of the corresponding particle sizes in a first range and the lengths of the pulses produced by the photodetecting means providing measurements of the particle sizes in a second range of particle sizes greater than said first range, and sizing means responsive to the measurements made by said measuring means to provide an indication of the sizes of the particles causing said pulses to be generated, the amplitude measurements made by said measuring means representing particle sizes in said first range in said indication and the length measurements made by said measuring means representing particle sizes in said second range in said indication.

2. An instrument for measuring a wide range of size of particles in a fluid, comprising a means to define a sample stream of fluid containing particles to be measured, means to direct a light beam through said sample stream, photodetecting means to detect light scattered from said beam in response to particles in said sample stream passing through said beam to generate a pulse in response to each particle passing through said beam, measuring means to measure the amplitude of each pulse produced by said photodetecting means and the length of each pulse produced by said photodetecting means, the amplitudes of the pulses produced by the photodetecting means providing measurements of the corresponding particle sizes in a first range and the lengths of the pulses produced by said photodetecting means providing measurements of the particle sizes in a second range, second photodetecting means to detect an unscattered portion of said beam passing through said sample stream and to generate pulses in response to each particle in said fluid stream passing through said beam, said measuring means being operable to measure the amplitude of pulses produced by said second photodetecting means, the amplitude of the pulses generated by aid second photodetecting means providing a measurement of the corresponding particle in a third range of particle sizes between said first range and said second range.

3. An instrument as recited in claim 2, wherein said first size range includes particles of 5 microns in diameter, said second size range includes particles 225 microns in diameter, and said third size range includes particles 30 microns in diameter, said instrument further comprising means to select amplitude measurements made by said measuring means of pulses produced by said first mentioned photodetecting means in response to particles in said first size range as measurements of particles in said first size range, to select amplitude measurements made by said measuring means of pulses produced by said second photodetecting means in response to particles in said third size range as measurements of particles in said third size range, and to select pulse length measurements of pulses produced by said first mentioned photodetecting means made by said measuring means in response to particles in said second size range as measurements of particles in said second size range microns.

4. An instrument for measuring a wide range of size of particles in a fluid, comprising a means to define a sample stream of fluid containing particles to be measured, means to direct a light beam through said sample stream, photodetecting means to detect light scattered from said beam in response to particles in said sample stream passing through said beam to generate a pulse in response to each particle passing through said beam, and measuring means to measure the amplitude of each pulse produced by said photodetecting means and the length of each pulse produced by said photodetecting means, the amplitudes of the pulses produced by the photodetecting means providing measurements of the corresponding particle sizes in a first range and the lengths of the pulses produced by said photodetecting means providing measurements of the particle sizes in a second range, said measuring means comprising pulse amplitude converting means to convert the amplitudes of pulses generated by said photodetecting means to digital values, and pulse length converting means to convert the pulse lengths of pulses produced by said photodetecting means to digital values.

5. An instrument recited in claim 4 further comprising memory having a multiplicity of storage locations, a separate storage location in a first set of said storage locations corresponding to each digital value produced by said pulse amplitude converting means and representing a particle size in said first range, a separate storage location in a second set of storage locations corresponding to each digital value produced by said pulse length converting means representing a particle size in said second range, and means to increment the storage location in said first set corresponding to each digital value produced by said pulse amplitude converting means in response to a particle in said first size range and to increment the storage location in said second set corresponding to each digital value produced by said pulse length converting means in response to a particle in said second size range.

6. An instrument for measuring a wide range of particle sizes of particles in a fluid comprising means to define a sample stream of fluid containing particles to be measured, means to direct a light beam through said sample stream of fluid, first photodetecting means to detect light scattered from said beam in response to particles passing through said beam in said sample stream and to generate a pulse in response to each particle passing through said beam, second photodetecting means to detect an unscattered portion of said beam passing through said sample stream and to generate a pulse in response to each particle in said particle stream passing through said beam, measuring means to measure the amplitudes of the pulses produced by said first and second photodetecting means, the amplitudes of the pulses produced by said first photodetecting means being used as a measurement of particles in a first size range and the amplitudes of the pulses produced by said second photodetecting means being used as measurement of particles in a second size range greater than said first size range.

7. An instrument as recited in claim 6, wherein said measuring means converts the amplitudes of pulses produced by said first and second photodetecting means to digital values.

8. An instrument as recited in claim 7 further comprising memory means having a multiplicity of storage locations, each storage location of a first set of said storage locations corresponding to a different digital value produced by said measuring means representing a particle size in said first range, each storage location of a second set of said storage locations corresponding to a different digital value produced by said measuring means representing a particle size in said second range, and means to increment the corresponding storage location in said first set in response to each digital value produced by said measuring means in response to a particle in said first size range and to increment the corresponding storage location in said second set in response to each digital value produced by said measuring means in response to a particle in said second size range.

9. An instrument for measuring a wide range of particle sizes of particles in a fluid comprising means defining a sample stream of fluid containing particles to be measured, means to direct a light beam through said sample stream, first photodetecting means to detect light scattered from said beam in response to particles in said sample stream passing through said beam and to generate a pulse in response to each particle passing through said beam, first measuring means to measure the lengths of pulses produced by first photodetecting means, second photodetecting means to detect an unscattered portion of said beam passing through said sample stream and to generate a pulse in response to each particle in said sample stream passing through said beam, second measuring means to measure the amplitudes of the pulses produced by said second photodetecting means, the lengths of the pulses produced by said first photodetecting means being used as a measurement of particles in a first size range and the amplitudes of the pulses produced by said second photodetecting means being used as a measurement of the particles in a second size range less than said first size range.

10. An instrument as recited in claim 9, wherein said first measuring means comprises means to convert the pulse length of each pulse produced by said first photodetecting means into a digital value and said second measuring means comprising means to convert the amplitude of each pulse produced by said second photodetecting means to a digital value.

11. An instrument as recited in claim 10 further comprising a memory means comprising a multiplicity of storage locations, each storage location of a first set of said storage locations corresponding to a different digital value produced by said first measuring means representing a particle size in said first size range, each storage location of a second set of said storage locations corresponding to a different digital value produced by said second measuring means representing a particle size in said second size range, and means to increment the corresponding storage location in said first set in response to each digital value produced by said first measuring means in response to a particle in said first size range and to increment the corresponding storage location in said second set in response to each digital value produced by said second measuring means in response to each particle in said second size range.

* * * * *